United States Patent
Wu et al.

(10) Patent No.: US 6,235,954 B1
(45) Date of Patent: May 22, 2001

(54) HYDROCARBON HYDROGENATION CATALYST AND PROCESS

(75) Inventors: An-hsiang Wu, Bartlesville; Charles A. Drake, Nowata, both of OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/408,824

(22) Filed: Sep. 29, 1999

(51) Int. Cl.⁷ .............................. C07C 5/05; C07C 7/163
(52) U.S. Cl. ..................... 585/260; 585/259; 208/144
(58) Field of Search ..................... 585/259, 260; 208/144

(56) References Cited

U.S. PATENT DOCUMENTS

| | | | |
|---|---|---|---|
| 3,113,983 | 12/1963 | Kirsch et al. | 260/677 |
| 3,865,750 | * 2/1975 | Rase et al. | 252/443 |
| 4,078,011 | 3/1978 | Glockner et al. | 260/677 |
| 4,260,840 | 4/1981 | Puls et al. | 585/259 |
| 5,330,944 | * 7/1994 | Sherif et al. | 502/64 |
| 5,646,085 | * 7/1997 | Jacquot et al. | 502/177 |
| 6,051,520 | * 4/2000 | Wu et al. | 502/60 |
| 6,090,274 | * 7/2000 | Wu et al. | 208/216 R |
| 6,093,671 | * 7/2000 | Wu et al. | 502/60 |

* cited by examiner

Primary Examiner—Bekir L. Yildirim
(74) Attorney, Agent, or Firm—Reece A. Scott

(57) ABSTRACT

A catalyst composition and process for preparing such catalyst composition which can be useful in contacting a hydrocarbon-containing fluid which contains a highly unsaturated hydrocarbon such as 1,3-butadiene, in the presence of hydrogen, with such catalyst composition in a hydrogenation zone under a hydrogenation condition effective to hydrogenate such highly unsaturated hydrocarbon to a less unsaturated hydrocarbon such as n-butene is disclosed. Such process for preparing a catalyst composition includes (1) combining a zeolite, a Group VIB metal, and an inorganic support to form a modified zeolite; (2) calcining such modified zeolite under a calcining condition to produce a calcined, modified zeolite; and (3) contacting such calcined, modified zeolite with a carburizing agent under a carburizing condition to provide such catalyst composition.

37 Claims, No Drawings

HYDROCARBON HYDROGENATION CATALYST AND PROCESS

BACKGROUND OF THE INVENTION

This invention relates to a catalyst composition, the preparation of a catalyst composition, and to a process of using a catalyst composition for hydrogenating a highly unsaturated hydrocarbon.

It is well known to one skilled in the art that an unsaturated hydrocarbon can be produced by a thermal cracking process. For example, a fluid stream containing a saturated hydrocarbon such as, for example, ethane, propane, butane, pentane, naphtha, or combinations thereof can be fed into a thermal (or pyrolytic) cracking furnace. Within the furnace, the saturated hydrocarbon is converted to a less unsaturated hydrocarbon such as, for example, ethylene and propylene. Less unsaturated hydrocarbons are an important class of chemicals that find a variety of industrial uses. For example, ethylene and propylene can be used as a monomer or comonomer for producing polyolefins. Other uses of less unsaturated hydrocarbons are well known to one skilled in the art.

However, a less unsaturated hydrocarbon produced by a thermal cracking process generally contains an appreciable amount of highly unsaturated hydrocarbons such as less desirable alkyne(s), diolefin(s), polyene(s), or combinations thereof. For example, ethylene produced by thermal cracking of ethane is generally contaminated with some acetylene which must be selectively hydrogenated to ethylene, but not to ethane, in a hydrogenation reaction. Similarly, in a thermal cracking process for producing a butene, butynes and butadienes are generally co-produced which must be selectively hydrogenated to a butene, but not further hydrogenated to a butane.

These highly unsaturated hydrocarbons described above are undesirable for several reasons. Generally, these highly unsaturated hydrocarbons are highly reactive and tend to polymerize by forming gums if they are left in the product stream. Also, these undesirable products can have an effect on further processes, such as alkylation. Thus, these highly unsaturated hydrocarbons are preferably removed. A preferred process for removing such undesirable highly unsaturated hydrocarbons is a selective hydrogenation process. This process not only minimizes the loss of desired less unsaturated hydrocarbons, but can also help to avoid a "runaway" reaction which is difficult to control in front-end and total-cracked-gas processes thereby increasing the selectivity by which desired products, as opposed to undesired products, are produced.

Catalysts comprising palladium and an inorganic support are known catalysts for the hydrogenation of highly unsaturated hydrocarbons such as alkynes and/or diolefins. Sulfided catalysts comprising a metal selected from the group consisting of molybdenum, cobalt, and nickel and combinations thereof have also been used as hydrogenation catalysts. However, these catalysts can be expensive to prepare and can have the potential to introduce sulfur contaminants which can poison and deactivate catalysts used in hydrogenation processes.

As such, development of a catalyst which is cost-efficient and easier to prepare than known catalysts and processes therewith in the selective hydrogenation of a highly unsaturated hydrocarbon such as a diolefin to a less unsaturated hydrocarbon such as a monoolefin in which selectivity is improved and unnecessary introduction of contaminants is avoided would be a significant contribution to the art and to the economy.

SUMMARY OF THE INVENTION

It is an object of this invention to provide a catalyst composition which can be useful as a catalyst in the selective hydrogenation of a highly unsaturated hydrocarbon such as a diolefin to a less unsaturated hydrocarbon such as a monoolefin.

It is another object of this invention to provide a process for producing such catalyst composition which can be useful as a catalyst in the selective hydrogenation of a highly unsaturated hydrocarbon such as a diolefin to a less unsaturated hydrocarbon such as a monoolefin.

It is another object of this invention to employ such catalyst composition in a process for selectively hydrogenating a highly unsaturated hydrocarbon such as a diolefin to a less unsaturated hydrocarbon such as a monoolefin.

Advantages of this invention include a catalyst composition which avoids unnecessary introduction of contaminants which can poison and deactivate catalysts used in hydrogenation processes. Another advantage of this invention is that the process of making such catalyst is cost-efficient and easier to prepare than known catalysts. Yet another advantage of this invention is an increased or enhanced selectivity to a desired product such as a less unsaturated hydrocarbon.

The present invention is directed to a catalyst composition which comprises a carburized, calcined, modified zeolite having incorporated therein a metal of Group VIB of the Periodic Table of the Elements (i.e., a Group VIB metal) such as chromium, molybdenum, tungsten and combinations thereof. The composition also comprises an inorganic support. The inorganic support can be selected from the group consisting of silica, alumina, titanium dioxide, zirconia, a spinel such as zinc aluminate, zinc titanate, magnesium aluminate, calcium aluminate, and the like and combinations thereof.

The present invention is also directed to a process for producing a catalyst composition which can be useful as a catalyst in the selective hydrogenation of a highly unsaturated hydrocarbon such as a diolefin to a lower unsaturated hydrocarbon such as a monoolefin. The process can comprise: (1) combining a zeolite, a metal of Group VIB of the Periodic Table of the Elements (i.e., a Group VIB metal), and an inorganic support to form a modified zeolite; (2) calcining such modified zeolite under a calcining condition to produce a calcined, modified zeolite; and (3) contacting such calcined, modified zeolite with a carburizing agent under a carburizing condition to provide a carburized, calcined, modified zeolite.

The present invention is also directed to a process which can be used to employ a catalyst composition of this invention in the selective hydrogenation of a highly unsaturated hydrocarbon such as a diolefin to a less unsaturated hydrocarbon such as a monoolefin. The process can comprise contacting a hydrocarbon-containing fluid, which comprises a highly unsaturated hydrocarbon, in the presence of hydrogen with a catalyst composition in a hydrogenation zone under a hydrogenation condition effective to selectively hydrogenate a highly unsaturated hydrocarbon to a less unsaturated hydrocarbon. The catalyst composition can be a catalyst composition of the present invention.

Other objects and advantages of the invention will be apparent from the detailed description of the invention and the appended claims.

DETAILED DESCRIPTION OF THE INVENTION

As used in the present invention, the term "hydrocarbon" generally refers to, unless otherwise indicated, one or more hydrocarbons, saturated or unsaturated, having in the range of from about 1 carbon atom per molecule to about 50 carbon atoms per molecule, preferably in the range of from about 2 carbon atoms per molecule to about 40 carbon atoms per molecule, more preferably in the range of from about 2 carbon atoms per molecule to about 30 carbon atoms per molecule and, most preferably, in the range of from about 2 carbon atoms per molecule to about 20 carbon atoms per molecule. Preferably, a hydrocarbon is a saturated hydrocarbon, a mixture of saturated hydrocarbons, or a mixture of saturated hydrocarbons and less unsaturated hydrocarbons. Also, as used in the present invention, the term "fluid" denotes gas, liquid, vapor, or combinations thereof.

The term "saturated hydrocarbon" refers to any hydrocarbon which does not contain any carbon-to-carbon double bonds or carbon-to-carbon triple bonds. Examples of saturated hydrocarbons include, but are not limited to, ethane, propane, butanes, hexanes, octanes, decanes, naphtha, and the like and combinations thereof.

The term "highly unsaturated hydrocarbon" refers to a hydrocarbon having a carbon-to-carbon triple bond or two or more carbon-to-carbon double bonds. Examples of highly unsaturated hydrocarbons include, but are not limited to, aromatic compounds such as benzene and naphthalene; alkynes such as acetylene, propyne (also referred to as methylacetylene), and butynes; diolefins such as propadiene, butadienes, pentadienes (including isoprene), hexadienes, octadienes, and decadienes; and the like and combinations thereof.

The term "less unsaturated hydrocarbon" refers to a hydrocarbon in which a carbon-to-carbon triple bond in a highly unsaturated hydrocarbon is hydrogenated to a carbon-to-carbon double bond, or a hydrocarbon in which the number of carbon-to-carbon double bonds is one less, or at least one less, than that in a highly unsaturated hydrocarbon, or a hydrocarbon having at least one carbon-to-carbon double bond. Examples of less unsaturated hydrocarbons include, but are not limited to, monoolefins such as ethylene, propylene, butenes, pentenes, hexenes, octenes, decenes, and the like and combinations thereof.

The term "hydrogenation process" refers to a process which hydrogenates a highly unsaturated hydrocarbon such as an alkyne or a diolefin to a less unsaturated hydrocarbon such as a monoolefin or a saturated hydrocarbon such as an alkane. The term "selective" refers to such hydrogenation process in which a highly unsaturated hydrocarbon such as an alkyne or a diolefin is hydrogenated to a less unsaturated hydrocarbon such as a monoolefin without fuirther hydrogenating such less unsaturated hydrocarbon to a saturated hydrocarbon such as an alkane. Thus, for example, when a highly unsaturated hydrocarbon is converted to a less unsaturated hydrocarbon without further hydrogenating such a less unsaturated hydrocarbon to a saturated hydrocarbon, the hydrogenation process is "more selective" than when such highly unsaturated hydrocarbon is hydrogenated to a less unsaturated hydrocarbon and then further hydrogenated to a saturated hydrocarbon.

The term "n-butenes" refers to 1-butenes, cis-2-butenes, and trans-2-butenes.

According to the present invention, a catalyst composition which can be useful as a catalyst in the selective hydrogenation of a highly unsaturated hydrocarbon such as a diolefin to a less unsaturated hydrocarbon such as a monoolefin is provided. The composition can comprise a carburized, calcined, modified zeolite wherein the modified zeolite comprises a zeolite, a Group VIB metal selected from the group consisting of chromium, molybdenum, tungsten, and combinations thereof, and an inorganic support. Examples of suitable inorganic supports include, but are not limited to, silica, alumina, titanium dioxide, zirconia, a spinel such as zinc aluminate, zinc titanate, magnesium aluminate, calcium aluminate, and the like and combinations thereof. The presently preferred inorganic support is an alumina selected from the group consisting of alpha alumina, beta alumina, delta alumina, eta alumina, gamma alumina, and the like and combinations thereof. The more preferred inorganic support is gamma alumina. The composition can also comprise a carburized, calcined, modified zeolite wherein the modified zeolite is a mixture or an extruded mixture comprising a zeolite, a Group VIB metal, and an inorganic support.

Any commercially available zeolite can be employed in the present invention as long as such zeolite is effective in selectively hydrogenating a highly unsaturated hydrocarbon to a less unsaturated hydrocarbon when used according to the present invention. The presently preferred zeolites are beta zeolite, zeolite X, zeolite Y, zeolite L, and the like and combinations thereof. The more preferred zeolite is zeolite L.

Generally, the catalyst composition can comprise a metal of Group VIB of the Periodic Table of the Elements (i.e., a Group VIB metal) in any weight percent so long as such weight percent is effective in selectively hydrogenating a highly unsaturated hydrocarbon such as a diolefin to a less unsaturated hydrocarbon such as a monoolefin. The catalyst composition comprises a Group VIB metal in the range of from about 1 weight percent Group VIB metal based on the total weight of the catalyst composition to about 95 weight percent Group VIB metal, preferably in the range of from about 5 weight percent Group VIB metal to about 80 weight percent Group VIB metal and, more preferably, in the range of from about 10 weight percent Group VIB metal to about 60 weight percent Group VIB metal.

Generally, the catalyst composition can comprise a zeolite in any weight percent so long as such weight percent is effective in selectively hydrogenating a highly unsaturated hydrocarbon such as a diolefin to a less unsaturated hydrocarbon such as a monoolefin. The catalyst composition comprises a zeolite in the range of from about 1 weight percent zeolite based on the total weight of the catalyst composition to about 95 weight percent zeolite, preferably in the range of from about 5 weight percent zeolite to about 80 weight percent zeolite and, more preferably, in the range of from about 10 weight percent zeolite to about 60 weight percent zeolite.

Generally, the catalyst composition can comprise an inorganic support in any weight percent so long as such weight percent is effective in selectively hydrogenating a highly unsaturated hydrocarbon such as a diolefin to a less unsaturated hydrocarbon such as a monoolefin. The catalyst composition comprises an inorganic support in the range of from about 1 weight percent inorganic support based on the total weight of the catalyst composition to about 90 weight percent inorganic support, preferably in the range of from about 5 weight percent inorganic support to about 80 weight percent inorganic support and, more preferably, in the range of from about 10 weight percent inorganic support to about 60 weight percent inorganic support.

Generally, the catalyst composition can comprise carbon in any weight percent so long as such weight percent is effective in selectively hydrogenating a highly unsaturated hydrocarbon such as a diolefin to a less unsaturated hydrocarbon such as a monoolefin. The catalyst composition comprises carbon in the range of from about 0.1 weight percent carbon based on the total weight of the catalyst composition to about 90 weight percent carbon, preferably in the range of from about 0.5 weight percent carbon to about 60 weight percent carbon and, more preferably, in the range of from about 1 weight percent carbon to about 50 weight percent carbon.

Any metal of Group VIB of the Periodic Table of the Elements (i.e., a Group VIB metal) such as chromium, molybdenum, tungsten, and the like and combinations thereof can be employed in the present invention. The presently preferred Group VIB metal is molybdenum. Preferably, when preparing a catalyst composition disclosed herein, such Group VIB metal is present in a Group VIB metal-containing compound. Preferably, such Group VIB metal or Group VIB metal-containing compound is selected such that it can be combined with, or incorporated therein or thereon, a zeolite, or a zeolite and an inorganic support, of the present invention. And, preferably, such Group VIB metal or Group VIB metal-containing compound is selected so that, as compared to use of a zeolite only, or zeolite and inorganic support only, it is more effective in a catalyst composition of the present invention in selectively hydrogenating a highly unsaturated hydrocarbon such as a diolefin to a less unsaturated hydrocarbon such as a monoolefin.

Generally, any molybdenum compound which, when combined with a zeolite, or a zeolite and an inorganic support, according to the present invention, is effective in selectively hydrogenating a highly unsaturated hydrocarbon such as a diolefin to a less unsaturated hydrocarbon such as a monoolefin can be used in the present invention. Examples of suitable molybdenum compounds include, but are not limited to, molybdenum chloride, molybdenum acetate, molybdenum fluoride, molybdenum hexacarbonyl, molybdenum sulfide, sodium molybdates, potassium molybdates, molybdenum oxychloride, molybdenum sulfide, ammonium tetrathiomolybdate, ammonium molybdate, ammonium dimolybdate, ammonium heptamolybdate, molybdenum oxides, and the like and combinations thereof. The molybdenum can have any suitable oxidation state such as 2, 3, 4, 5, and 6. The presently preferred molydenum compound is molybdenum oxide.

Generally, any tungsten compound which, when combined with a zeolite, or a zeolite and an inorganic support, according to the present invention, is effective in selectively hydrogenating a highly unsaturated hydrocarbon such as a diolefin to a less unsaturated hydrocarbon such as a monoolefin can be used in the present invention. Examples of suitable tungsten compounds include, but are not limited to, tungsten hexachloride, tungsten tetrachloride, tungsten pentachloride, tungsten hexabromide, tungsten tetrabromide, tungsten pentabromide, tungsten hexafluoride, tungsten tetrafluoride, tungsten pentafluoride, tungsten hexacarbonyl, tungsten oxychloride, tungsten hexasulfide, tungsten tetrasulfide, tungsten oxide, tungsten pentasulfide, ammonium metatungstate, sodium metatungstate, potassium metatungstate, tungstic acid and the like and combinations thereof. The presently preferred tungsten compound is tungsten oxide.

Generally, any chromium compound which, when combined with a zeolite, or a zeolite and an inorganic support, according to the present invention, is effective in selectively hydrogenating a highly unsaturated hydrocarbon such as a diolefin to a less unsaturated hydrocarbon such as a monoolefin can be used in the present invention. Examples of suitable chromium compounds include, but are not limited to, chromium acetate, chromium acetylacetonate, chromium chloride, chromium fluoride, chromium nitrate, hydrated chromium nitrate, chromium nitrate nonahydrate, chromium nitride, chromium oxide, chromium perchlorate, chromium potassium sulfate, chromium sulfate, chromium telluride, and the like and combinations thereof. The presently preferred chromium compound is chromium oxide.

The catalyst composition can be in any physical form and dimension so long as such physical form and dimension is effective in selectively hydrogenating a highly unsaturated hydrocarbon such as a diolefin to a less unsaturated hydrocarbon such as a monoolefin. Generally, the catalyst composition can be characterized by characteristics such as shape, particle size, and surface area. The catalyst composition can have any suitable shape such as spherical, cylindrical, trilobal, and the like and combinations thereof. The catalyst composition can have a particle size generally in the range of from about 1 millimeter (mm) to about 10 mm, preferably in the range of from about 2 mm to about 8 mm. Generally, the catalyst composition can have a surface area, as measured by the BET method (Brunauer, Emmett and Teller method) employing $N_2$ in the range of from about 0.6 $m^2/g$ to about 200 $m^2/g$, preferably in the range of from about 1 $m^2/g$ to about 100 $m^2/g$.

According to the present invention, any suitable inorganic support can be used so long as the catalyst composition can selectively hydrogenate a highly unsaturated hydrocarbon such as a diolefin to a less unsaturated hydrocarbon such as a monoolefin. Examples of suitable inorganic supports include, but are not limited to, silica, alumina, titanium dioxide, zirconia, a spinel such as zinc aluminate, zinc titanate, magnesium aluminate, calcium aluminate, and the like and combinations thereof. The presently preferred inorganic support is an alumina selected from the group consisting of alpha alumina, beta alumina, delta alumina, eta alumina, gamma alumina, and the like and combinations thereof. The more preferred inorganic support is gamma alumina.

According to the present invention, a process for producing a catalyst composition which can be useful as a catalyst composition in the hydrogenation of a highly unsaturated hydrocarbon such as a diolefin to a less unsaturated hydrocarbon such as a monoolefin is provided. The catalyst composition can be prepared by any suitable, effective method or manner which results in a catalyst composition comprising a zeolite, a Group VIB metal, and an inorganic support wherein such catalyst composition has been calcined and carburized, and can also be prepared by any method or manner which results in the catalyst composition being effective in the selective hydrogenation of a highly unsaturated hydrocarbon to a less unsaturated hydrocarbon.

The process of preparing the catalyst composition can comprise (1) combining a zeolite, a Group VIB metal, and an inorganic support to form a modified zeolite; (2) calcining such modified zeolite under a calcining condition to produce a calcined, modified zeolite; and (3) contacting such calcined, modified zeolite with a carburizing agent under a carburizing condition to provide a catalyst composition. Generally, the combining of a zeolite, a Group VIB metal, and an inorganic support can be conducted in any suitable manner and in any suitable order which results in a modified zeolite which can then be calcined and carburized to produce a catalyst composition of the present invention. Generally, the amounts of a zeolite, a Group VIB metal, and an inorganic support used are such that when such zeolite, Group VIB metal, and inorganic support are combined, calcined, and carburized according to the present invention, a catalyst composition is produced having weight percents of zeolite, Group VIB metal, and inorganic support as disclosed hereinabove.

Any method or manner known to one skilled in the art for carrying out the combining of the combining step (1) to form a modified zeolite can be employed in this invention. Generally, the combining step can be any effective method to provide a modified zeolite so long as such modified zeolite can be calcined and carburized to produce a catalyst composition which is effective in selectively hydrogenating a highly unsaturated hydrocarbon such as a diolefin to a less unsaturated hydrocarbon such as a monoolefin. The term "modified zeolite" refers to a composition containing a zeolite, a Group VIB metal, and an inorganic support which can then be calcined and carburized according to the present invention to thereby provide the catalyst composition of the present invention. For example, the term "modified zeolite" can refer to a mixture of a zeolite, a Group VIB metal, and an inorganic support, an extruded mixture of a zeolite, a Group VIB metal, and an inorganic support, or a dried extruded mixture of a zeolite, a Group VIB metal, and an inorganic support.

For example, combining a zeolite, a Group VIB metal, and an inorganic support can comprise physically mixing or blending a Group VIB metal or Group VIB metal-containing compound with a zeolite and an inorganic support by stirring, extrusion, blending, kneading, and the like and combinations thereof. Also for example, a Group VIB metal or Group VIB metal-containing compound can be combined with a zeolite and an inorganic support by extrusion. The presently preferred technique for combining a zeolite, a Group VIB metal, and an inorganic support to thereby provide a modified zeolite which can be calcined and carburized to thereby provide a catalyst composition of the present invention is by physical mixing such zeolite in powder form, a Group VIB metal or Group VIB metal-containing compound in powder form, and an inorganic support in powder form to thereby provide a mixture which is then extruded.

Generally, any suitable means for mixing a zeolite, a Group VIB metal, and an inorganic support can be employed. Examples of suitable mixing means for use in preparing a mixture of a zeolite, a Group VIB metal, and an inorganic support of the inventive method are described in detail in *Perry's Chemical Engineers' Handbook*, Sixth Edition, published by McGraw-Hill, Inc., copyright 1984, at pages 21–3 through 21–10, which pages are incorporated herein by reference. Thus, examples of suitable mixing means can include, but are not limited to, devices such as tumblers, stationary shells or troughs, muller mixers, which are either batch type or continuous type, impact mixers, and the like. It is preferred to use a muller mixer in the physical mixing of a zeolite, a Group VIB metal, and an inorganic support. A liquid such as, but not limited to, water, may be used in the mixing of a zeolite, a Group VIB metal, and an inorganic support to thereby provide a mixture.

The mixture of a zeolite, a Group VIB metal, and an inorganic support can then be formed or shaped, preferably extruded. Any suitable means known to those skilled in the art for forming or shaping, preferably extruding, the mixture of a zeolite, a Group VIB metal, and an inorganic support can be used to achieve the desired formed or shaped mixture, preferably an extruded mixture (i.e., extrudate). A liquid such as, but not limited to, water, may be used in forming or shaping, preferably extruding, the mixture of a zeolite, a Group VIB metal, and an inorganic support to thereby provide a formed or shaped, preferably extruded, mixture.

Generally, any suitable extruding means for extruding can be used to provide an extruded mixture of a zeolite, a Group VIB metal, and an inorganic support. Examples of suitable extruding means are described in detail in *Perry's Chemical Engineers' Handbook*, Sixth Edition, published by McGraw Hill, Inc., copyright 1984, at pages 8–60 through 8–72, which pages are incorporated herein by reference. Thus, examples of suitable extruding means include, but are not limited to, such devices as screw extruders (also known as auger extruders or auger-type extruders) and the like and combinations thereof. It is presently preferred to use a screw extruder in the extruding of a mixture of a zeolite, a Group VIB metal, and an inorganic support.

The mixture, preferably an extruded mixture of a zeolite, a Group VIB metal, and an inorganic support can be subjected to a drying condition in an atmosphere of air or inert gas (such as, but not limited to, nitrogen, hydrogen, argon, and the like and combinations thereof) by any method(s) or manner known to one skilled in the art. Such drying condition includes a temperature in the range of from about 200° C. to about 1200° C., preferably a temperature in the range of from about 400° C. to about 1000° C. and, most preferably, a temperature in the range of from about 500° C. to about 900° C. Such drying condition also includes a pressure in the range of from about 7 pounds per square inch absolute (psia) upwardly to about 750 psia, preferably a pressure in the range of about 14 psia upwardly to about 450 psia and, most preferably, a pressure in the range of from about atmospheric pressure (i.e, about 14.7 psia) upwardly to about 25 psia. The drying of the mixture can also be carried out under vacuum conditions. Such drying condition also includes a time period in the range of from about 0.5 hour to about 40 hours, preferably in the range of from about 1 hour to about 30 hours and, most preferably, in the range of from about 1.5 hours to about 20 hours. The rate of drying the mixture is controlled so as to avoid surges of water vapor and splattering.

The modified zeolite, preferably a mixture of a zeolite, a Group VIB metal, and an inorganic support, more preferably an extruded mixture, most preferably a dried extruded mixture, can then be calcined under a calcining condition by any method(s) or manner known to one skilled in the art to give a calcined, modified zeolite. Generally, such calcining condition is such as to suitably provide a calcined, modified zeolite which can be carburized according to the present invention to produce a catalyst composition which is effective in selectively hydrogenating a highly unsaturated hydrocarbon such as a diolefin to a less unsaturated hydrocarbon such as a monoolefin. Preferably, the modified zeolite is calcined in air.

Generally, such calcining condition includes a temperature in the range of from about 100° C. to about 1500° C., preferably in the range of from about 200° C. to about 800° C. and, most preferably, in the range of from about 250° C. to about 700° C. Such calcining condition also includes a pressure in the range of from about 7 pounds per square inch absolute (psia) to about 750 psia, preferably in the range of from about atmospheric pressure (i.e., about 14.7 psia) to about 450 psia and, most preferably, in the range of from about atmospheric pressure to about 150 psia. Such calcining condition also includes a time period in the range of from about 1 hour to about 30 hours, preferably in the range of from about 2 hours to about 20 hours and, most preferably, in the range of from about 3 hours to about 15 hours.

The calcined, modified zeolite can then be contacted with a carburizing agent under a carburizing condition by any method(s) or manner known to one skilled in the art to thereby provide a catalyst composition of the present invention.

Generally, any aliphatic hydrocarbon, straight-chained hydrocarbon, branch-chained hydrocarbon, or aromatic hydrocarbon, nonsubstituted or substituted, can be used as the carburizing agent. However, it is preferred that the hydrocarbon contains in the range of from about 1 carbon atom per molecule to about 20 carbon atoms per molecule, preferably in the range of from about 1 carbon atom per molecule to about 15 carbon atoms per molecule and, most preferably, in the range of from about 1 carbon atom per molecule to about 10 carbon atoms per molecule. Examples of a suitable hydrocarbon for use as a carburizing agent in the present invention include, but are not limited to, methane, ethane, propane, butanes, isobutane, pentanes, hexanes, heptanes, octanes, nonanes, benzene, toluene, and the like and combinations thereof. The presently preferred hydrocarbon for use as a carburizing agent in the present invention is methane. The quantity of hydrocarbon required for use as a carburizing agent is a quantity that can result in a carburized, calcined, modified zeolite or a catalyst composition of the present invention having a weight percent of carbon as disclosed hereinabove. The quantity of carbon which is incorporated with the catalyst composition of the present invention can be determined by any means known to one skilled in the art such as, for example, thermal gravimetric analysis.

Generally, such carburizing condition is such as to suitably provide a catalyst composition which is effective in selectively hydrogenating a highly unsaturated hydrocarbon such as a diolefin to a less unsaturated hydrocarbon such as a monoolefin. The carburizing condition for contacting the calcined, modified zeolite with a carburizing agent includes a temperature in the range of from about 150° C. to about 1500° C., preferably in the range of from about 200° C. to about 1200° C. and, most preferably, in the range of from about 275° C. to about 1000° C. Such carburizing condition also includes a pressure that can accommodate the temperature ranges, preferably about atmospheric pressure (i.e., about 14.7 pounds per square inch), and a time period in the range of from about 1 hour to about 40 hours, preferably in the range of from about I hour to about 20 hours and, most preferably, in the range of from about 1.5 hours to about 15 hours. The carburizing agent is delivered at a flow rate generally in the range of from about 25 milliliters per minute (mL/min) to about 500 mL/min, preferably in the range from about 50 mL/min to about 400 mL/min and, most preferably, in the range of from about 75 mL/min to about 300 mL/min.

Preferably, the carburizing is carried out in the presence of a gas that is inert to the contacting of the calcined, modified zeolite and carburizing agent, such as hydrogen, helium, argon, nitrogen, and combinations thereof. The presently preferred inert gas is hydrogen delivered at a hydrogen flow rate in the range of from about 200 mL/min to about 1200 mL/min, preferably at a hydrogen flow rate in the range of from about 250 mL/min to about 1000 mL/min and, most preferably, at a hydrogen flow rate in the range of from about 300 mL/min to about 800 mL/min.

According to the present invention, a process for selectively hydrogenating a highly unsaturated hydrocarbon such as a diolefin to a less unsaturated hydrocarbon such as a monoolefin is provided. The process can comprise contacting a hydrocarbon-containing fluid which comprises one or more highly unsaturated hydrocarbons such as an alkyne(s) and/or diolefin(s) with the catalyst composition disclosed herein in the presence of hydrogen in a hydrogenation zone under a hydrogenation condition to selectively hydrogenate such one or more highly unsaturated hydrocarbons to a less unsaturated hydrocarbon such as monoolefin.

Hydrogen can be present either in the hydrocarbon-containing fluid or in a hydrogen-containing fluid which is mixed with the hydrocarbon-containing fluid before contacting with the catalyst composition disclosed herein. If a hydrogen-containing fluid is used, it can be a substantially pure hydrogen or any fluid containing a sufficient concentration of hydrogen to effect the hydrogenation disclosed herein. It can also contain other gases such as, for example, nitrogen, methane, carbon monoxide, carbon dioxide, steam, or combinations thereof so long as the hydrogen-containing fluid contains a sufficient concentration of hydrogen to effect the hydrogenation disclosed herein.

Optionally, the catalyst composition can be first treated, prior to the hydrogenation disclosed herein, with a hydrogen-containing fluid to activate the catalyst composition. Such reductive, or activation, treatment can be carried out at a temperature generally in the range of from about 20° C. to about 500° C., preferably in the range of from about 30° C. to about 450° C. and, most preferably, in the range of from 30° C. to about 400° C. for a time period in the range of from about 1 minute to about 30 hours, preferably in the range of from about 0.5 hour to about 25 hours and, most preferably, in the range of from 1 hour to 20 hours at a pressure generally in the range of from about 1 pound per square inch absolute to about 1000 pounds per square inch absolute (psia), preferably in the range of from about 14.7 psia to about 500 psia and, most preferably, in the range of from 14.7 psia to 200 psia. When this optional reductive treatment is not carried out, the hydrogen gas present in the reaction medium accomplishes this reduction during the initial phase of the hydrogenation process(es) of this invention.

The highly unsaturated hydrocarbon(s) is generally present in the hydrocarbon-containing fluid as an impurity generally at a level found in typical commercial feed streams. The highly unsaturated hydrocarbon(s) is generally present in the hydrocarbon-containing fluid in the range of from about 1 part by weight highly unsaturated hydrocarbon (s) per billion parts by weight hydrocarbon-containing fluid (i.e., about 1 ppb) to about 50,000 parts by weight highly unsaturated hydrocarbon(s) per million parts by weight hydrocarbon-containing fluid (i.e., about 50,000 ppm), typically at a level in the range of from about 10 ppb to about 40,000 ppm and, most typically, at a level in the range of from about 100 ppb to about 30,000 ppm.

The hydrocarbon-containing fluid of the selective hydrogenation process of this invention can also comprise one or more less unsaturated hydrocarbon(s) such as a monoolefin (s), one or more saturated hydrocarbon(s) such as an alkane (s), and one or more aromatic hydrocarbons such as benzene, toluene, ethylbenzene, styrene, xylenes, and combinations thereof These additional hydrocarbons can be present in the hydrocarbon-containing fluid at a level in the range of from about 0.001 weight percent to about 99.999 weight percent.

Examples of suitable alkynes include, but are not limited to, acetylene, propyne (also referred to as methylacetylene), 1-butyne, 2-butyne, 1-pentyne, 2-pentyne, 3-methyl-1-butyne, 1-hexyne, 1-heptyne, 1-octyne, 1-nonyne, 1-decyne, and the like and combinations thereof. The presently preferred alkynes are acetylene and propyne.

The alkynes are primarily hydrogenated to the corresponding alkenes. For example, acetylene is primarily hydrogenated to ethylene; propyne is primarily hydrogenated to propylene; and the butynes are primarily hydrogenated to the corresponding butenes (e.g., n-butenes).

Examples of suitable diolefins include those containing in the range of from 3 carbon atoms per molecule to about 12 carbon atoms per molecule. Examples of suitable diolefins include, but are not limited to, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene (also known as tricyclo[5.2.1]$^{2,6}$deca-3,8-diene), and the like and combinations thereof.

Presently preferred diolefins are propadiene, 1,2-butadiene, 1,3-butadiene, isoprene, 1,2-pentadiene, 1,3-pentadiene, 1,4-pentadiene, cyclopentadienes (such as 1,3-cyclopentadiene), dicyclopentadiene (also known as tricyclo [5.2.1]$^{2,6}$deca-3,8-diene), and combinations thereof. These diolefins are preferably selectively hydrogenated to their corresponding monoolefins containing the same number of carbon atoms per molecule as the diolefins. For example, propadiene is selectively hydrogenated to propylene; 1,2-butadiene and 1,3-butadiene are selectively hydrogenated to n-butenes; 1,3-pentadiene and 1,4-pentadiene are selectively hydrogenated to 1-pentene and 2-pentene; isoprene is selectively hydrogenated to methyl-1-pentene and methyl-2-pentene; and 1,3-cyclopentadiene is selectively hydrogenated to cyclopentene. The more presently preferred diolefin is 1,3-butadiene.

Examples of suitable monoolefins include, but are not limited to, ethylene, propylene, n-butenes (also referred to as normal butenes which include 1-butenes, cis-2-butenes, and trans-2-butenes), isobutylene, 1-pentene, 2-pentene, methyl-1-butene (such as 2-methyl-1-butene), methyl-2-butene (such as 2-methyl-2-butene), 1-hexene, 2-hexene, 3-hexene, methyl-1-pentene, 2,3-dimethyl-1-butene, 1-heptene, 2-heptene, 3-heptene, methyl-1-hexene, methyl-2-hexene, methyl-3-hexene, dimethylpentenes, ethylpentenes, octenes, methylheptenes, dimethylhexenes, ethylhexenes, nonenes, methyloctenes, dimethylheptenes, ethylheptenes, trimethylhexeneg, cyclopentenes, cyclohexenes, methylcyclopentenes, cycloheptenes, methylcyclohexenes, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and the like and combinations thereof.

Examples of suitable saturated hydrocarbons include, but are not limited to, methane, ethane, propane, butanes, methylpropanes, methylbutanes, dimethylbutanes, pentanes, hexanes, and the like and combinations thereof.

Examples of suitable aromatic hydrocarbons include, but are not limited to, benzene, toluene, ethylene, styrene, xylenes, and the like and combinations thereof.

Furthermore, the hydrocarbon-containing fluid can contain in the range of from about 0.001 weight percent hydrogen to about 20 weight percent hydrogen, and up to 10,000 parts per million by volume (ppmv) of carbon monoxide.

It is within the scope of this invention to have additional compounds (such as water, alcohols, ethers, aldehydes, ketones, carboxylic acids, esters and other oxygenated compounds) present in the hydrocarbon-containing fluid, as long as such additional compounds do not significantly interfere with the selective hydrogenation process of a highly unsaturated hydrocarbon to a less unsaturated hydrocarbon as described herein.

In a preferred embodiment of the present invention, the hydrocarbon-containing fluid contains 1,3-butadiene and essentially no other hydrocarbons. In other words, the hydrocarbon-containing fluid is a 1,3-butadiene stream. Preferably, the 1,3-butadiene is selectively hydrogenated to n-butenes (i.e., normal butenes which include 1-butenes, cis-2-butenes, and trans-2-butenes) without further hydrogenating such n-butenes to butane.

The selective hydrogenation process(es) of this invention is generally carried out by contacting a hydrocarbon-containing fluid comprising at least one highly unsaturated hydrocarbon, in the presence of hydrogen, with a catalyst composition of this invention under a hydrogenation condition. The hydrocarbon-containing fluid can be contacted by any suitable manner with a catalyst composition described herein which is contained within a hydrogenation zone. Such hydrogenation zone can comprise, for example, a reactor vessel.

The contacting step, of contacting the hydrocarbon-containing fluid with a catalyst composition disclosed herein, can be operated as a batch process step or, preferably, as a continuous process step. In the latter operation, a solid or fixed catalyst bed or a moving catalyst bed or a fluidized catalyst bed can be employed. Preferably, a fixed catalyst bed is employed. Any of these operational modes have advantages and disadvantages, and those skilled in the art can select the one most suitable for a particular hydrocarbon-containing fluid and catalyst composition.

The contacting step is preferably carried out within a hydrogenation zone, wherein is contained a catalyst composition disclosed herein, and under a hydrogenation condition that suitably promotes the selective hydrogenation of a highly unsaturated hydrocarbon to a less unsaturated hydrocarbon as described herein. Such hydrogenation condition should be such as to avoid significant hydrogenation of a less unsaturated hydrocarbon(s) being initially present in the hydrocarbon-containing fluid to a saturated hydrocarbon(s) such as an alkane(s) or cycloalkane(s).

Generally, such hydrogenation process comprises the presence of hydrogen, preferably hydrogen gas, in an amount in the range of from about 0.1 mole of hydrogen employed for each mole of highly unsaturated hydrocarbon present in the hydrocarbon-containing fluid to about 1000 moles of hydrogen employed for each mole of highly unsaturated hydrocarbon present in the hydrocarbon-containing fluid, preferably in the range of from about 0.5 mole to about 500 moles of hydrogen employed for each mole of highly unsaturated hydrocarbon present in the hydrocarbon-containing fluid and, most preferably, in the range of from about 0.7 mole to about 200 moles of hydrogen employed for each mole of highly unsaturated hydrocarbon present in the hydrocarbon-containing fluid.

Generally, such hydrogenation condition comprises a temperature and a pressure necessary for the selective hydrogenation process of this invention depending largely upon the activity of the catalyst composition, the hydrocarbon-containing fluid composition, and the desired extent of hydrogenation. Generally, such temperature is in the range of from about 10° C. to about 600° C., preferably in the range of from about 20° C. to about 500° C. and, most preferably, in the range of from 30° C. to 450° C. A suitable pressure is generally in the range of from about 0 pounds per square inch gauge (psig) to about 2000 psig, preferably in the range of from about 0 psig to about 1500 psig and, most preferably, in the range of from about 0 psig to about 1000 psig.

Such hydrogenation condition further comprises the flow rate at which the hydrocarbon-containing fluid is charged (i.e., the charge rate of hydrocarbon-containing fluid) to the hydrogenation zone. The flow rate is such as to provide a gas hourly space velocity ("GHSV") generally exceeding 1 liter/liter/hour. The term "gas hourly space velocity", as used herein, shall mean the numerical ratio of the rate at which a hydrocarbon-containing fluid is charged to the hydrogenation zone in liters per hour at standard condition of temperature and pressure ("STP") divided by the liters of catalyst composition contained in the hydrogenation zone to which the hydrocarbon-containing fluid is charged. Typically, the gas hourly space velocity of the hydrocarbon-containing fluid will be in the range of from about 1 to about 30,000 liters of hydrocarbon-containing fluid per liter of catalyst per hour (liter/liter/hour), preferably in the range of from about 2 to about 20,000 liter/liter/hour and, most preferably, in the range of from about 3 to about 10,000 liter/liter/hour.

If it is desired to regenerate the catalyst composition of this invention after prolonged use in the selective hydrogenation process(es) described herein, the regeneration can be accomplished by calcining the catalyst composition in an oxidizing atmosphere such as in air at a temperature that does not exceed about 700° C. to burn off carbonaceous and sulfur deposits.

The following examples are presented to further illustrate this invention and are not to be construed as unduly limiting the scope of this invention.

EXAMPLE I

This example illustrates the preparation of various molybdenum-containing catalysts to be used in a selective hydrogenation process.

Catalyst A (Control) A 15.0 gram quantity of molybdenum oxide ($MoO_3$) in powder form was combined with 25.0 grams of a commercially available alumina ($Al_2O_3$) support in powder form (such alumina support had been provided by United Catalyst Inc. (UCI), Louisville, Ky. under the product designation of "CATAPAL D") by physically mixing the $MoO_3$ and the CATAPAL D. The mixture was then extruded to provide an extrudate having a diameter of 1/16 inch (i.e., a 1/16 inch extrudate). The molybdenum-and-alumina extrudate was then calcined in air at 539° C. for 6 hours to produce 30.8 grams of Control Catalyst A. Control Catalyst A contained 30.8 weight percent molybdenum (Mo).

Catalyst B (Control) A 22.4 gram quantity of the above-described Control Catalyst A was heated, in a gas mixture of methane ($CH_4$) and hydrogen ($H_2$) at a hydrocarbon (methane, $CH_4$) flow rate of 150 mL/min and a hydrogen ($H_2$) flow rate of 600 mL/min, from a temperature of 400° C. to 705° C. over a time period of 5 hours followed by heating at 700° C. for 2 hours to provide 21.0 grams of Control Catalyst B. Control Catalyst B contained 66 weight percent molybdenum carbide ($MO_2C$). X-ray data confirmed that the molybdenum carbide had a hexagonal structure and a crystalline domain size of 8 angstoms. The "crystalline domain size" was determined from the line broadening of the X-ray diffraction profile.

Catalyst C (Invention) A 5.0 gram quantity of molybdenum oxide ($MoO_3$) in powder form was combined with 12.0 grams of a commercially available alumina ($Al_2O_3$) support in powder form (such alumina support had been provided by United Catalyst Inc. (UCI), Louisville, Ky. under the product designation of "CATAPAL D") and 1.0 gram of commercially available zeolite L in powder form (such zeolite L had been provided by CU Chemie Uetikon AG, Switzerland, under the product designation "K-LTL ZEOCAT") by physically mixing the $MoO_3$, CATAPAL D, and zeolite L. The mixture was then extruded to provide an extrudate having a diameter of 1/16 inch (i.e., a 1/16 inch extrudate). The molybdenum-alumina-zeolite extrudate was then calcined in air at 538° C. for 6 hours to produce 21.5 grams of a modified zeolite. A 20.3 gram quantity of such modified zeolite was then heated, in a gas mixture of methane ($CH_4$) and hydrogen ($H_2$) at a hydrocarbon (methane, $CH_4$) flow rate of 150 mL/min and a hydrogen ($H_2$) flow rate of 600 mL/min, from a temperature of 400° C. to 705° C. over a time period of 5 hours followed by heating at 700° C. for 2 hours to provide 19.0 grams of Invention Catalyst C. Invention Catalyst C contained 70 weight percent molybdenum carbide ($Mo_2C$). X-ray data confirmed that the molybdenum carbide had a hexagonal structure and a crystalline domain size of 7 angstoms. The "crystalline domain size" was determined from the line broadening of the X-ray diffraction profile.

EXAMPLE II

This example illustrates the performance of the catalysts described hereinabove in Example I in a selective hydrogenation process.

A 3.4 gram quantity of Control Catalyst A (the runs were repeated using a 3.3 gram quantity of Control Catalyst B and a 2.7 gram quantity of Invention Catalyst C) was placed in a stainless steel reactor tube having a 0.62 inch inner diameter and a length of about 18 inches. The catalyst (resided in the middle of the reactor, both ends of the reactor were packed with 6 mL of 3 mm glass beads) was reduced at about 380° C. for about 1 hour under hydrogen gas flowing at 12 liters per hour at 0 pounds per square inch gauge (psig). Thereafter, while maintaining a hydrogen gas flow rate of 6 liters per hour (L/hr) at 0 psig, a hydrocarbon-containing fluid containing 1,3-butadiene having a density of 2.204 gram per milliliter (g/mL) and a molecular weight of 54.07 was continuously introduced into the reactor at a rate of about 6.0 L/hr (resulting in a weight hourly space velocity ("WHSV") of about 4 to 5 hour$^{-1}$). The hydrogen gas flow rate was such as to maintain a hydrogen to highly unsaturated hydrocarbon (1,3-butadiene) (H2:HC) mole ratio of about 1. The reactor was then heated to a reaction temperature of about 370° C. over about an 8-hour time period for Control Catalyst A and Invention Catalyst C. A reaction temperature of 300° C. was used for Control Catalyst B because at 300° C. all 1,3-butadiene present in the hydrocarbon-containing fluid had been converted. The formed reaction product exited the reactor tube and passed through several ice-cooled traps. The liquid portion remained in these traps and was weighed, whereas the volume of the gaseous portion which exited the traps was measured in a "wet test meter". Liquid and gaseous product samples (collected at hourly intervals) were analyzed by means of a gas chromatograph. Results of test runs for Catalysts A, B, and C are summarized in Table I. All test data were obtained after about 7 hours on stream.

Various n-butenes selectivities for each of the above-described catalysts are shown below in Table I. The term "1,3-butadiene weight percent conversion" refers to the weight percent of the feed (1,3-butadiene) which was hydrogenated to a hydrocarbon other than 1,3-butadiene. The term "n-butenes (or $\Sigma C_4=$) selectivity" refers to the mole percent of feed (1,3-butadiene) which was hydrogenated to the desired n-butenes (1-butenes, cis-2-butenes, and trans-2-butenes). The n-butenes selectivity value is representative of the amount of desired n-butenes (1-butenes, cis-2-butenes, and trans-2-butenes) contained in the process effluent as opposed to undesired product, i.e., butane. Thus, a higher value for n-butenes selectivity indicated that less butane was produced and that the catalyst was more selective or had a better selectivity to n-butenes.

TABLE I

| Catalyst | Catalyst Preparation | Time on Stream (hr) | Temp (° C.) | 1,3-BD wt % conversion[d] | n-butenes (or $\Sigma C_4=$) mole % selectivity[e] |
|---|---|---|---|---|---|
| Catalyst A (Control)[a] | MoO$_3$ + alumina (Calcined) | 7.14 | 371 | 48.9 | 78.4 |
| Catalyst B (Control)[b] | MoO$_3$ + alumina (Calcined and Carburized) | 7.00 | 301 | 100.0 | 13.8 |
| Catalyst C (Invention)[c] | MoO$_3$ + alumina + zeolite L (Calcined and Carburized) | 7.15 | 376 | 96.2 | 98.0 |

[a]Catalyst A (Control) MoO$_3$ was combined with alumina and then calcined.
[b]Catalyst B (Control) MoO$_3$ was combined with alumina and then calcined and carburized.
[c]Catalyst C (Invention) MoO$_3$ was combined with alumina and a zeolite L and then calcined and carburized.
[d]1,3-BD wt % conversion represents the weight percent of the feed (1,3-butadiene) that was hydrogenated.
[e]n-butenes (or $\Sigma C_4=$) mole % selectivity represents the mole percent of 1,3-butadiene which was converted to the desired n-butenes (1-butenes, cis-2-butenes, and trans-2-butenes) contained in the process effluent as opposed to undesired product such as butane.

Test data in Table I clearly show that Invention Catalyst C produced less undesirable product, i.e., butane, than Control Catalysts A and B. In other words, Invention Catalyst C had better selectivity to n-butenes than Control Catalysts A or B. For example, at a 1,3-butadiene conversion of 96.2 weight percent, Invention Catalyst C was already at 98.0 mole percent selectivity to n-butenes whereas Control Catalyst B, after 100.0 weight percent of the 1,3-butadiene was converted, produced a mere 13.8 mole percent selectivity to n-butenes. In addition, Control Catalyst A exhibited a better mole percent selectivity to n-butenes (78.4) than Control Catalyst B, but only converted 48.9 weight percent of the 1,3-butadiene. The data demonstrate that Invention Catalyst C is clearly superior in attaining a high weight percent conversion of 1,3-butadiene (96.2) while attaining a very high mole percent selectivity to n-butenes (98.0).

The performance of Invention Catalyst C, as compared to Control Catalysts A and B, is superior in hydrogenating a highly unsaturated hydrocarbon such as 1,3-butadiene to a less unsaturated hydrocarbon such as n-butenes (1-butenes, cis-2-butenes, and trans-2-butenes) without further hydrogenating to a saturated hydrocarbon such as butane. The improvement in catalyst performance is believed to be due to the novel process of using a catalyst composition prepared by combining a zeolite, a Group VIB metal, and an inorganic support to provide a modified zeolite which is then calcined and carburized.

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

What is claimed is:

1. A process comprising contacting a hydrocarbon-containing fluid which comprises a highly unsaturated hydrocarbon, in the presence of hydrogen, with a catalyst composition in a hydrogenation zone under a hydrogenation condition effective to hydrogenate said highly unsaturated hydrocarbon to a less unsaturated hydrocarbon wherein said catalyst composition is prepared by the steps comprising:
    (1) combining a zeolite, a Group VIB metal, and an inorganic support to form a modified zeolite;
    (2) calcining said modified zeolite under a calcining condition to produce a calcined, modified zeolite; and
    (3) contacting said calcined, modified zeolite with a carburizing agent under a carburizing condition to provide said catalyst composition.

2. A process according to claim 1 wherein said highly unsaturated hydrocarbon is a diolefin.

3. A process according to claim 2 wherein said diolefin contains in the range of from 3 carbon atoms per molecule to about 12 carbon atoms per molecule.

4. A process according to claim 3 wherein said diolefin is selected from the group consisting of propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene (also known as tricyclo[5.2.1 ]$^{2,6}$deca-3,8-diene), and combinations thereof.

5. A process according to claim 4 wherein said diolefin is selected from the group consisting of propadiene, 1,2-butadiene, 1,3-butadiene, isoprene, 1,2-pentadiene, 1,3-pentadiene, 1,4-pentadiene, cyclopentadienes, dicyclopentadiene (also known as tricyclo[5.2.1 ]$^{2,6}$deca-3,8-diene), and combinations thereof.

6. A process according to claim 5 wherein said diolefin is selected from the group consisting of 1,2-butadiene and 1,3-butadiene.

7. A process according to claim 6 wherein said diolefin is 1,3-butadiene.

8. A process according to claim 1 wherein said less unsaturated hydrocarbon is selected from the group consisting of ethylene, propylene, n-butenes, isobutylene, 1-pentene, 2-pentene, methyl-1-butenes, methyl-2-butenes, 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and combinations thereof.

9. A process according to claim 8 wherein said less unsaturated hydrocarbon comprises n-butenes.

10. A process according to claim 1 wherein said hydrocarbon-containing fluid further comprises a monoolefin.

11. A process according to claim 10 wherein said monoglefin is selected from the group consisting of ethylene, propylene, n-butenes, isobutylene, 1-pentene, 2-pentene, methyl-1-butenes, methyl-2-butenes, 1-hexene, 2-hexene, 3-hexene, methyl-1-pentenes, 2,3-dimethyl-1-butene, 1-heptene, 2-heptene, 3-heptene, methyl-1-hexenes, methyl-2-hexynes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and combinations thereof.

12. A process according to claim 11 wherein said hydrocarbon-containing fluid further comprises a saturated hydrocarbon selected from the group consisting of methane, ethane, propane, butane, methylpropane, methylbutane, dimethylbutane, pentanes, hexanes, and combinations thereof.

13. A process according to claim 12 wherein said hydrocarbon-containing fluid further comprises an aromatic hydrocarbon selected from the group consisting of benzene, toluene, ethylbenzene, styrene, xylenes, and combinations thereof.

14. A process according to claim 1 wherein said hydrogenation condition comprises:
the presence of hydrogen in an amount in the range of from about 0.1 to about 1000 moles of said hydrogen employed for each mole of said highly unsaturated hydrocarbon present in said hydrocarbon-containing fluid.
a temperature in the range of from about 10° C. to about 600° C.;
a pressure in the range of from about 0 pounds per square inch gauge (psig) to about 2000 psig; and
a charge rate of said hy drocarbon-containing fluid to said hydrogenation zone such as to provide a gas hourly space velocity in the range of from about 1 to about 30,000 liters of hydrocarbon-containing fluid per liter of catalyst per hour (liter/liter/hour).

15. A process according to claim 14 wherein said hydrogenation zone comprises a reactor vessel.

16. A process according to claim 1 wherein said combining of said combining step (1) comprises mixing said zeolite, said Group VIB metal, and said inorganic support to form a mixture and then extruding said mixture to form said modified zeolite.

17. A process according to claim 16 wherein said mixing comprises subjecting said zeolite, said Group VIB metal, and said inorganic support to a mixing means to provide said mixture.

18. A process according to claim 17 wherein said mixing means is selected from the group consisting of tumblers, stationary shells or troughs, muller mixers, impact mixers, and combinations thereof.

19. A process according to claim 18 wherein said mixing means comprises a muller mixer.

20. A process according to claim 16 wherein said extruding comprises subjecting said mixture to an extruding means to provide an extruded mixture.

21. A process according to claim 20 wherein said extruding means is selected from the group consisting of screw extruders, auger extruders, augyer-type extruders, and combinations thereof.

22. A process according to claim 21 wherein said extruding means comprises a screw extruder.

23. A process according to claim 1 wherein said catalyst composition comprises said zeolite in an amount in the range of from about 1 weight percent said zeolite based on the total weight of said catalyst composition to about 95 weight percent, said catalyst composition comprises said Group VIB metal in an amount in the range of from about 1 weight percent said Group VIB metal based on the total weight of said catalyst composition to about 95 weight percent, and said catalyst composition comprises said inorganic support in an amount in the range of from about 1 weight percent said inorganic support based on the total weight of said catalyst composition to about 90 weight percent.

24. A process according to claim 1 wherein said calcining condition comprises:
a temperature in the range of from about 100° C. to about 1500° C.;
a time period in the range of from about 1 hour to about 30 hours; and
a pressure in the range of from about 7 pounds per square inch absolute (psia) to about 750 psia.

25. A process according to claim 1 wherein said carburizing agent comprises a hydrocarbon.

26. A process according to claim 25 wherein said hydrocarbon contains in the range of from about 1 carbon atom per molecule to about 20 carbon atoms per molecule.

27. A process according to claim 26 wherein said hydrocarbon is selected from the group consisting of methane, ethane, propane, butanes, isobutane, pentanes, hexanes, heptanes, octanes, nonanes, benzene, toluene, and combinations thereof.

28. A process according to claim 27 wherein said hydrocarbon is methane.

29. A process according to claim 1 wherein said carburizing condition comprises:
the presence of hydrogen delivered at a hydrogen flow rate in the range of from about 200 mL/min to about 1200 mL/min;
a temperature in the range of from about 150° C. to about 1500° C.;
a time period in the range of from about 1 hour to about 40 hours;
and said carburizing agent is delivered at a flow rate in the range of from about 25 mL/min to about 500 mL/min.

30. A process according to claim 1 wherein said zeolite is selected from the group consisting of beta zeolite, zeolite X, zeolite Y, zeolite L, and combinations thereof.

31. A process according to claim 30 wherein said zeolite is zeolite L.

32. A process according to claim 1 wherein said group VIB metal is selected from the group consisting of chromium, molybdenum, tungsten, and combinations thereof.

33. A process according to claim 32 wherein said group VIB metal is molybdenum.

34. A process according to claim 33 wherein said molybdenum is present in a molybdenum compound selected from the group consisting of molybdenum chloride, molybdenum acetate, molybdenum fluoride, molybdenum hexacarbonyl, molybdenum sulfide, sodium molybdates, potassium molybdates, molybdenum oxychloride, molybdenum sulfide, ammonium tetrathiomolybdate, ammonium molybdate, ammonium dimolybdate, ammonium heptamolybdate, molybdenum oxides, and combinations thereof.

35. A process according to claim 34 wherein said molybdenum compound is molybdenum oxide.

36. A process according to claim 1 wherein said inorganic support is selected from the group consisting of silica, alumina, titanium dioxide, zirconia, spinel, and combinations thereof.

37. A process according to claim 36 wherein said inorganic support is an alumina selected from the group consisting of alpha alumina, beta alumina, delta alumina, eta alumina, gamma alumina, and combinations thereof.

* * * * *